(12) United States Patent
Dürrstein et al.

(10) Patent No.: US 11,986,579 B2
(45) Date of Patent: May 21, 2024

(54) DISINFECTION DEVICE AND COMPRESSOR SYSTEM, CONNECTION DEVICE AND TREATMENT DEVICE WITH SUCH A DEVICE

(71) Applicant: DÜRR DENTAL SE, Bietigheim-Bissingen (DE)

(72) Inventors: Martin Dürrstein, Bietigheim-Bissingen (DE); Andreas Hägele, Weinstadt (DE); Walter Bauer, Eberdingen-Nussdorf (DE); Jürgen Schmidtke, Königsbach-Stein (DE)

(73) Assignee: DÜRR DENTAL SE, Bietigheim-Bissingen (DE)

( * ) Notice: Subject to any disclaimer, the term of this patent is extended or adjusted under 35 U.S.C. 154(b) by 744 days.

(21) Appl. No.: 16/691,870

(22) Filed: Nov. 22, 2019

(65) Prior Publication Data
US 2020/0164099 A1 May 28, 2020

(30) Foreign Application Priority Data

Nov. 26, 2018 (DE) ...................... 10 2018 129 811.0

(51) Int. Cl.
*A61L 9/20* (2006.01)
*A61C 17/02* (2006.01)
(Continued)

(52) U.S. Cl.
CPC ............ *A61L 9/20* (2013.01); *A61C 17/0202* (2013.01); *A61C 17/022* (2013.01); *B01D 53/007* (2013.01); *A61L 2209/12* (2013.01)

(58) Field of Classification Search
None
See application file for complete search history.

(56) References Cited

U.S. PATENT DOCUMENTS 6,228,327 B1 * 5/2001 Matschke .................. A61L 9/20
250/436
2003/0086848 A1 5/2003 Saccomanno
(Continued)

FOREIGN PATENT DOCUMENTS

DE  10 2014 012 690   3/2016
DE  20 2016 104 823   11/2016
(Continued)

OTHER PUBLICATIONS

What is a Collimator?—Azo Optics. [online] [retrieved on Dec. 5, 2023]. pp. 1-2. https://www.azooptics.com/Article.aspx?ArticleID=541 (Year: 2013).*
(Continued)

*Primary Examiner* — Jelitza M Perez
(74) *Attorney, Agent, or Firm* — Chiesa Shahinian & Giantomasi PC

(57) ABSTRACT

A disinfection device with a pressure vessel which has an interior space for receiving a medium, and with at least one radiating device which is arranged such that it emits radiation into the interior space of the pressure vessel, wherein one or several surfaces of the interior space of the pressure vessel are formed at least partially as a reflection surface for the radiation. A particularly reliable sterilization of medical or dental compressed air in the pressure vessel is made possible. One or several disinfection devices according to the invention can be provided in a compressor system for providing compressed air for dental applications, in a dental treatment device with a compressed air device and/or in a connection device with one or several tube sections for guiding compressed air for dental applications.

20 Claims, 4 Drawing Sheets

(51) Int. Cl.
*A61C 17/022* (2006.01)
*B01D 53/00* (2006.01)

(56) References Cited

U.S. PATENT DOCUMENTS

| | | | |
|---|---|---|---|
| 2003/0170151 A1* | 9/2003 | Hunter | B01J 19/123 |
| | | | 588/303 |
| 2003/0190254 A1 | 10/2003 | Falat | |
| 2010/0291502 A1* | 11/2010 | Knight | A61C 17/0202 |
| | | | 433/29 |
| 2015/0165078 A1 | 6/2015 | Nevin | |
| 2016/0311699 A1 | 10/2016 | Burseth et al. | |
| 2017/0290933 A1 | 10/2017 | Collins et al. | |
| 2017/0296690 A1* | 10/2017 | Matsui | A61N 5/06 |

FOREIGN PATENT DOCUMENTS

| | | | | |
|---|---|---|---|---|
| JP | 2014061483 A | * | 4/2014 | C02F 1/325 |
| WO | 2003/039604 | | 5/2003 | |
| WO | 2005/011753 | | 2/2005 | |

OTHER PUBLICATIONS

Kenichiro, D. JP2014061483A—translated document (Year: 2014).*

* cited by examiner

DISINFECTION DEVICE AND COMPRESSOR SYSTEM, CONNECTION DEVICE AND TREATMENT DEVICE WITH SUCH A DEVICE

RELATED APPLICATIONS

The present application claims priority to German Application No. 10 2018 129 811.0 filed Nov. 26, 2018—the contents of which are fully incorporated herein by reference.

FIELD OF THE INVENTION

The invention relates to a disinfection device with at least one radiating device.

The invention also relates to a compressor system for providing compressed air for dental applications, a dental treatment device with a compressed air device, and a connection device with one or several tube sections for guiding compressed air for dental applications with such a disinfection device.

BACKGROUND OF THE INVENTION

A sterilizing device for sterilizing transport and processing surfaces with an illumination source is known from DE 20 2016 104 823 U1, wherein the illumination source comprises a tube body which comprises an emitting UV source with electrical connections. The sterilizing device described here works in an environment with indoor air. In addition, the sterilizing device described here with the corresponding illumination source is only designed for certain areas of application, such as textile cleaning.

DE 10 2014 012 690 discloses a water treatment device for a dental treatment unit, wherein the water is sterilized by ultrafiltration at an ultrafiltration filter.

In dental medicine, particularly high hygienic requirements are placed on products, operating supplies and materials. After all, dental compressed air is, among other things, also used in the treatment of the patient, for example for blowing out cavities or for cleaning teeth, e.g. when using powder jet devices. Depending on the application, the compressed air can come into direct contact with body orifices such as dental pockets or root canals. For this reason, a particularly high degree of hygiene is desirable particularly for dental compressed air.

In order to implement the hygienic requirements for dental compressed air, the use of bacteria filters in the intake air, of dry air systems and of particle filters is known. In the case of compressors for dental compressed air, it can be assumed that the compressed air produced is free of bacteria and viruses due to the high compression pressure and the high temperature during compression. The compressed air produced can, for example, be guided into a compressed air tank via a tubing, via one or several filters, via a cooler and a dry air system and stored there. Depending on the maintenance condition, function, downtimes and moisture content, it cannot be ruled out, for example, that the stored air is contaminated by germs in the compressed air tank. Under certain circumstances, retrograde air contamination by germs can also occur, which can be triggered coming from the dental treatment device, for example coming from lines or tubes in or on the treatment chair.

SUMMARY OF THE INVENTION

An object of the present invention is to provide at least a disinfection device which is further developed compared to the prior art and is particularly suitable for the sterilization of dental compressed air.

This object may be solved by a disinfection device of the type mentioned at the beginning, wherein the disinfection device comprises a pressure vessel with an interior space for receiving a medium, wherein the at least one radiating device of the disinfection device is arranged such that it emits radiation into the interior space of the pressure vessel, and wherein one or several surfaces of the interior space of the pressure vessel are formed at least partially as a reflection surface, preferably with a degree of reflection of more than 90%. According to the invention, a particularly reliable sterilization directly in the pressure vessel is made possible. Any bacteria or viruses present in the pressure vessel can be killed, whereby, for example, retrograde contamination by germs can also be reliably counteracted. The invention makes it possible to sterilize a medium with a defined volume flow and a corresponding flow velocity particularly reliably.

Preferably, the at least one radiating device can comprise a UVC radiation source. In this way, a particularly reliable and at the same time environmentally friendly disinfection is made possible. Such a disinfection device can also be effective without the use of chemicals.

It is advantageous if the at least one radiating device comprises an LED as a radiation source. An LED as a radiation source is characterized by a high operating safety and is particularly suitable for use in the medical or dental field.

It can be appropriate that the radiation source of the radiating device is arranged in a concave mirror. In this way, the radiation characteristic can be improved.

The radiating device is preferably designed such that a principal direction component of the emitted radiation is aligned parallel to a longitudinal axis of the pressure vessel. In this way, the disinfection effect of the radiation can be increased.

It is advantageous if the at least one radiation source is arranged in the region of a first side of the interior space, wherein a second side, opposite this first side, of the interior space comprises a reflection surface for the radiation. In this way, it is possible to prevent the radiation emitted by the at least one radiation source from being absorbed to a large extent at the side of the pressure vessel, the side being opposite of the radiation source.

In a further advantageous design, at least two sides of the interior space opposite to one another comprise reflection surfaces for the radiation.

For suitable alignment of the radiation in the pressure vessel, it is advantageous if at least one of the reflection surfaces is formed in the form of a concave mirror.

It is advantageous if at least one reflection surface is formed by a reflection layer applied to a substrate.

Reflection losses can be kept to a minimum if the reflection layer is at least partially made of aluminium.

In an advantageous design, the pressure vessel is designed as a tank with at least one passage for the inflow and outflow of the medium.

In another advantageous design, the pressure vessel is designed as a tubular pressure container with two or more passages for the medium.

Preferably, the pressure vessel is configured as a compressed air vessel for dental compressed air.

An object of the invention is also solved by a compressor system for providing compressed air for dental applications with a disinfection device designed according to the invention or one of its designs. The significant advantages thereby result by analogy with the advantages of the disinfection device.

The object underlying the invention may also solved by a dental treatment device with a compressed air device comprising a disinfection device designed according to the invention or one of its designs. The significant advantages thereby result by analogy with the advantages of the disinfection device.

The object underlying the invention may also solved by a connection device with one or several tube sections for guiding compressed air for dental applications, wherein at least one tube section comprises a disinfection device designed according to the invention or one of its designs. The significant advantages thereby result by analogy with the advantages of the disinfection device.

Other advantages and aspects of the present invention will become apparent upon reading the following description of the drawings and detailed description of the invention.

BRIEF DESCRIPTION OF THE DRAWINGS

Further advantageous designs of the invention result from the following description. Embodiments of the invention are thereby explained in more detail based on the drawing, without being limited to this. They show in simplified, schematic illustrations the following.

DETAILED DESCRIPTION OF THE PRESENT INVENTION

While this invention is susceptible to embodiments in many different forms, there is described in detail herein, preferred embodiments of the invention with the understanding that the present disclosures are to be considered as exemplifications of the principles of the invention and are not intended to limit the broad aspects of the invention to the embodiments illustrated.

Figure 1:
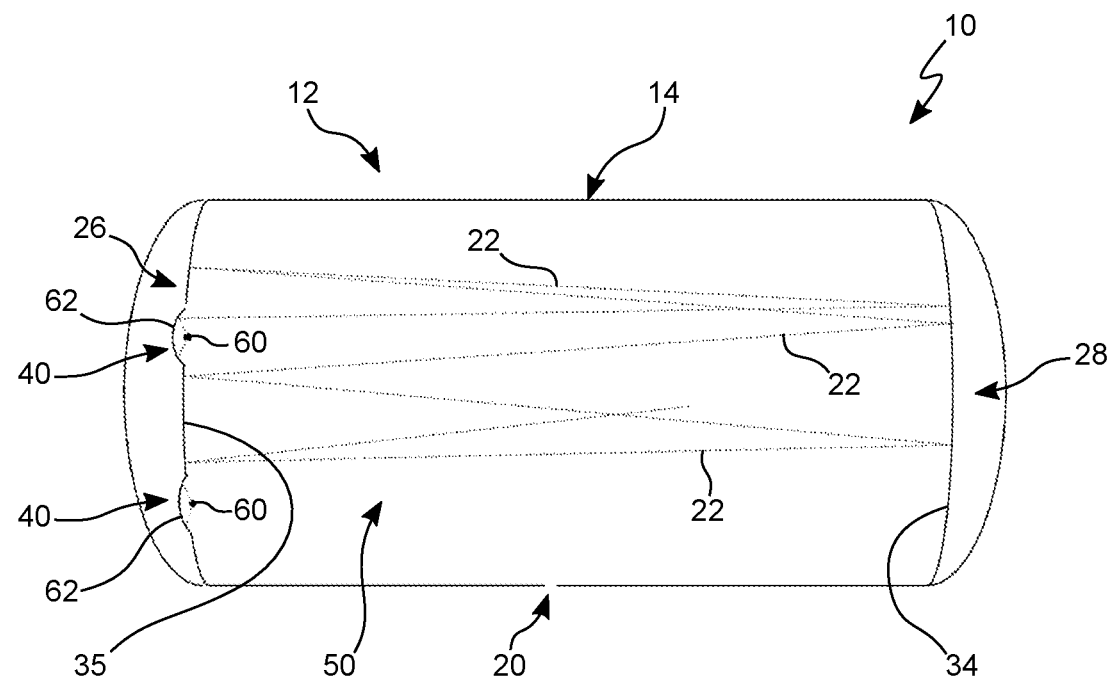
FIG. 1 shows an embodiment of a disinfection device according to the invention in a sectional view.
Figure 2:
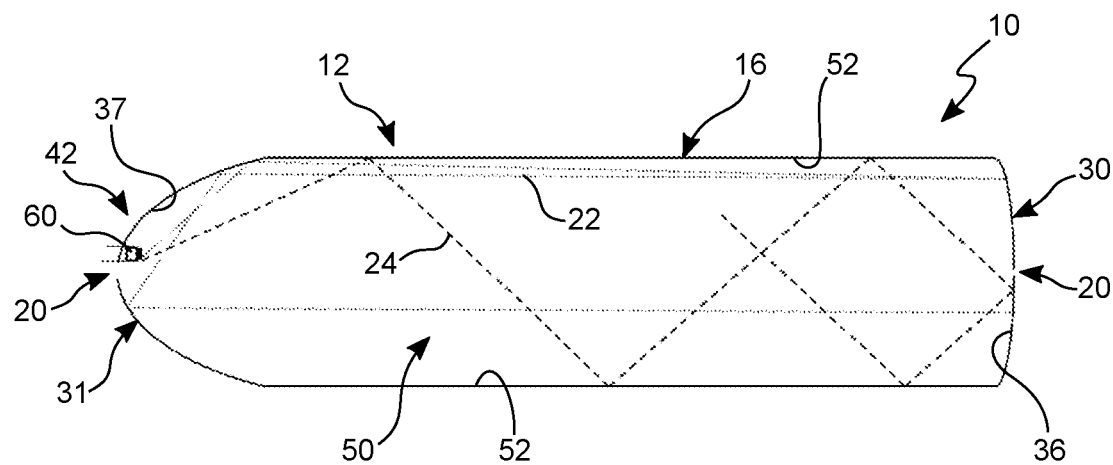
FIG. 2 shows a further embodiment of a disinfection device according to the invention in a sectional view.
Figure 3:
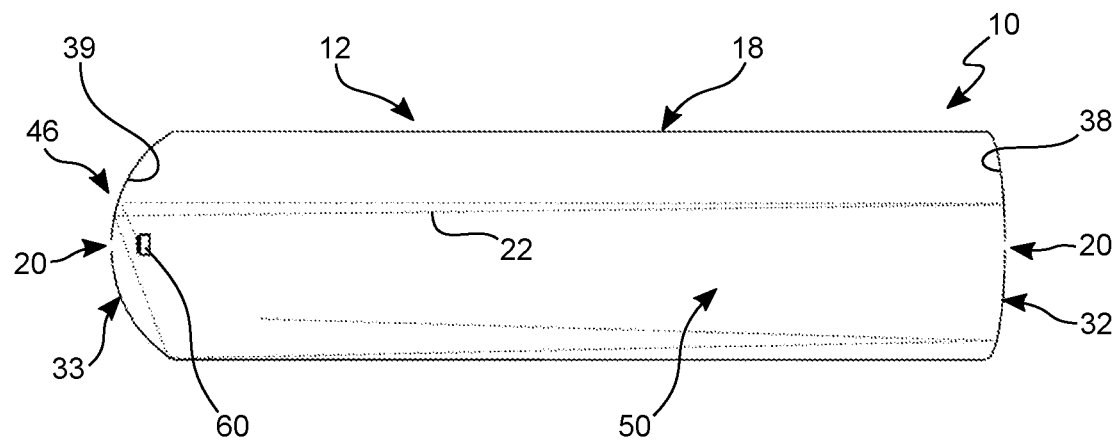
FIG. 3 shows a further embodiment of a disinfection device according to the invention in a sectional view.

FIGS. 1 to 3 show examples of a disinfection device 10 for the disinfection of a medium, such as air or liquid, in the interior space 50 of a pressure vessel 12. The disinfection device 10 is particularly suitable for compressed air used in medicine or dental medicine. FIGS. 1 to 3 show, as an example, pressure vessels 12, which are preferably configured as compressed air vessels for dental compressed air.

FIG. 1 shows a pressure vessel 12, which is advantageously suitable as a pressure accumulator on a compressor. FIGS. 2 and 3, on the other hand, show pressure vessels 12, which are advantageously suitable for installation in a treatment chair or in connection devices.

The disinfection devices 10 shown as examples in FIGS. 1 to 3 are equipped with radiating devices 40, 42, or 46 respectively such that a directed radiation is injected into the interior space 50 of the respective pressure vessel 12 through the radiating devices 40, 42 or 46 respectively. The pressure vessels 12 comprise reflection surfaces 34, 35, 36, 37, 38, 39, 52 in their interior space 50 for reflection of the injected radiation. Some ray paths 22 of the radiation emitted by the radiating devices 40, 42, 44, 46 are indicated in FIGS. 1 to 3 as an example. For the sake of clarity, the ray paths 22 are not provided with reference signs throughout in the drawings.

FIG. 1 shows a disinfection device 10 with a pressure vessel 12 designed as a tank 14. In the example shown, the pressure vessel 12 is a compressed air tank with a passage 20 for introducing and discharging air. The tank 14 is substantially cylindrical and comprises at both of its two end sides a bottom part 26, 28 respectively. The bottom parts 26, 28 can, for example, be designed as so-called dished bottoms. As a compressed air tank for dental medicine, the tank 14 can, for example, have a volume of approximately 60 litres to approximately 90 litres. The tank 14 shown in the example has a length which is considerably greater than its diameter. In the example, the length of the tank 14 is approximately twice the diameter.

In the example shown in FIG. 1, several radiating devices 40 are provided in the region of the first bottom part 26. The radiating devices 40 shown each comprise a radiation source 60 which radiates into the pressure vessel 12. UVC radiation sources, preferably UVC LEDs, can be used as radiation sources 60.

In order to achieve an disinfection effect as great as possible within the pressure vessel 12 (i.e. in particular to irradiate a large mass of air), the radiation is reflected at least substantially in the longitudinal direction between opposing reflection surfaces 34, 35, preferably back and forth several times. These reflection surfaces 34, 35 are arranged on the inner sides of the bottom parts 28, 26 respectively. Corresponding ray paths 22 are indicated in the drawing. Preferably, the reflection surfaces 34, 35 each form a concave mirror. By means of the previously described reflection of the emitted radiation, a significant increase in effectiveness is achieved. The increase in effectiveness is particularly great if the radiation covers as long a distance as possible between its reflection points and thus the probability of photons hitting the microorganisms is multiplied.

As indicated in the drawing, the radiating devices 40 can each comprise a reflector 62 for the radiation source 60. The reflector 62 can preferably be designed as a concave mirror, e.g. a parabolic mirror. In the example shown, the radiation sources 60 are each arranged in an inner reflector 62, i.e. in the reflector 62 of the radiation source 60. This inner reflector 62 is for its part arranged in an outer reflector which is formed by the reflection surface 35 on the inner side of the bottom part 26 of the pressure vessel 12.

The pressure vessel 12 can comprise at least one inspection opening, not shown in the drawing, in order to allow access, when needed, to the at least one radiation source 60. Such an inspection opening can be arranged in the bottom part 26 behind the at least one radiation source 60. An electrical connection of the at least one radiation source 60 occurs preferably via the bottom part 26 behind the radiation source 60. The inspection opening can also be designed such that the radiation source 60 with its supply lines is fixed directly in the inspection opening in an installable and removable fashion.

In the embodiment shown in FIG. 1, the concave-mirror-shaped reflection surfaces 34, 35 form a sort of cage for the radiation in the interior space 50 of the pressure vessel 12. The radiation is mainly decayed by losses at the reflection surfaces 34, 35 or by absorption in the air and at the microorganisms. The concave mirrors are designed sufficiently spherical to ensure appropriate guidance of the radiation. Alternatively, a slightly aspherical shaping is also possible.

The aperture of the concave mirrors preferably corresponds approximately to the diameter of the pressure vessel 12, wherein even an aperture which is up to approximately 10% smaller is only slightly less favorable. The mirror radius of the concave mirrors is advantageously at least 1.5 times the length of the container, preferably 2 to 6 times the length of the container. Generally, it is also possible that the reflection surfaces of the bottom parts 26, 28 are planar. In this case, however, a higher ray parallelism of the radiating device is necessary in order to achieve a comparable multiplication of the disinfection effect.

FIGS. 2 and 3 each show a disinfection device 10 with a tubular pressure container 16, 18 respectively as a pressure vessel 12. The diameter of the pressure container 16, 18 respectively is reduced compared to the design as a tank 14 shown in FIG. 1. This makes it preferably suitable for installation in supply lines or in a treatment chair. Such tubular pressure containers 16, 18 can be substantially cylindrical. It is also possible that the pressure containers 16, 18 have a geometry substantially corresponding to a truncated cone, i.e. that their shell comprises an angle between the surface line and the longitudinal axis of the pressure container 16, 18.

The tubular pressure containers 16, 18 shown in FIGS. 2 and 3 each comprise two end parts 30 and 31, 32 and 33 respectively, which oppose each other. A passage 20 is arranged in each of the two end parts 30, 31 and 32, 33 respectively. A medium can be supplied to and/or discharged from the pressure container 16 or 18 via the passages 20. In the examples shown, the passages 20 are arranged centrally in the end parts 30, 31 and 32, 33 respectively.

The inner sides of the end parts 30, 31, 32, 33 are equipped with reflection surfaces 36, 37 and 38, 39 respectively. In the region of a first end part 31, 33 at least one radiating device 42 and 46 respectively is provided respectively. The first end part 31, 33 of the pressure containers 16 and 18 respectively comprises a curvature. The reflection surface 37 and 39 respectively arranged on the inner side of the first end part 31, 33 forms a concave mirror in the examples shown. The concave mirror can thereby preferably be in the form of a parabolic mirror. The second end part 30, 32 comprises a reflection surface 36 and 38 respectively, which, for example, can form a slightly curved or planar mirror surface for the radiation.

Overall, the geometry of the embodiment according to FIG. 1 is more favorable than that of the embodiments according to FIGS. 2 and 3. The multiplication effect for the radiation is greater in the embodiment shown in FIG. 1.

In the examples shown in FIGS. 2 and 3, in contrast to the example shown in FIG. 1, the radiation is reflected twice at the reflection surfaces 37 and 39 respectively and once at the reflection surface 36 and 38 respectively during each "pass", i.e. a total of three times instead of twice.

In the embodiment of the disinfection device 10 shown in FIG. 2, the radiation is reflected substantially more frequently at the shell of the pressure vessel 12 than in the embodiment according to FIG. 1. The more frequent reflection of the radiation weakens the radiation, whereby the disinfection effect is reduced. As an example, a ray path 24 with multiple reflection at the shell is indicated in FIG. 2 by a dashed line. In order to counteract a weakening of radiation on the shell of the pressure vessel 12, the inner side of the shell of the tubular pressure container 16 shown as an example in FIG. 2 is equipped with a reflection surface 52. In this way, the absorption of radiation on the inner side of the shell is counteracted.

The reflection surfaces 34, 35, 36, 37, 38, 39, 52 of the pressure vessels 12 shown in FIGS. 1 to 3 can be provided by a reflector layer applied to a substrate. A part of the housing of the pressure vessel 12, so for example a bottom part 26, 28 or an end part 30, 31, 32, 33 respectively of the pressure vessel 12, can thereby, if shaped accordingly, be used directly as the substrate or as a support for the substrate.

The reflector layer is preferably made of aluminium. Aluminium, as pure as possible, is particularly well suited as a reflection material for UVC radiation, particularly for radiation with a wavelength range between approximately 250 nm and approximately 290 nm. An additional protective layer can be provided if necessary, in order to improve the durability.

In order to optimize production costs, for example in the case of the reflection surfaces 52, which are arranged on the inner side of the shell or of the middle part respectively of a tubular pressure container 16 as shown in FIG. 2, it may be useful to use polished steel, stainless steel and/or aluminium with or without a protective layer respectively for the production of the reflection surfaces 52, The reflection surfaces 34, 35, 36, 37, 38, 39, 52 can, for example, be produced by installing mirror foils and/or mirror sheets. The reflection surfaces 34, 35, 36, 37, 38, 39, 52 can, for example, also be produced by vapor deposition of the surfaces in the interior of the pressure vessel 12.

A pressure vessel 12 in the form of a tank 14 (see FIG. 1), in particular a compressed air tank, can, for example, be produced with a rolled and welded steel sheet as the middle part and with deep-drawn, so-called dished bottoms as end parts 31, 33 on the outer sides, wherein the dished bottoms are welded to the middle part. The middle part forms the shell of the tank 14, which is substantially cylindrical in shape. The compressed air tank is preferably painted internally for corrosion protection, for example by means of a lance.

The reflection surfaces 34, 35 can, for example, be produced such that the at least one reflection layer formed is connected to the dished bottoms, e.g. by spot welding. If necessary, the at least one reflection layer is provided with a protective foil at the relevant position. This protective foil can, for example, be removed from an inspection opening after welding the two dished bottoms to the inner part of the tank and, if necessary, after subsequent internal painting. Alternatively, the at least one reflection layer can be vapor deposited after welding the pressure vessel 12. If necessary, the pressure vessel 12 can be evacuated and the coating sources are introduced through one or several inspection openings.

Figure 4:
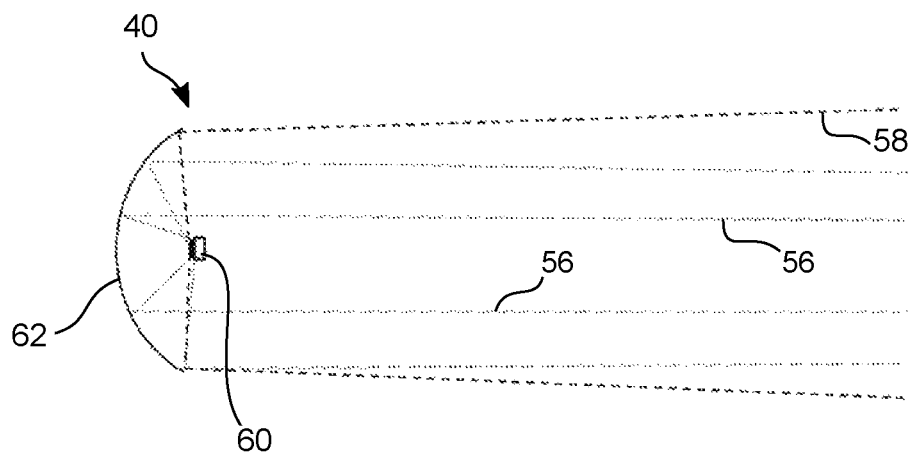
FIG. 4 shows a radiating device in a sectional view.
Figure 5:
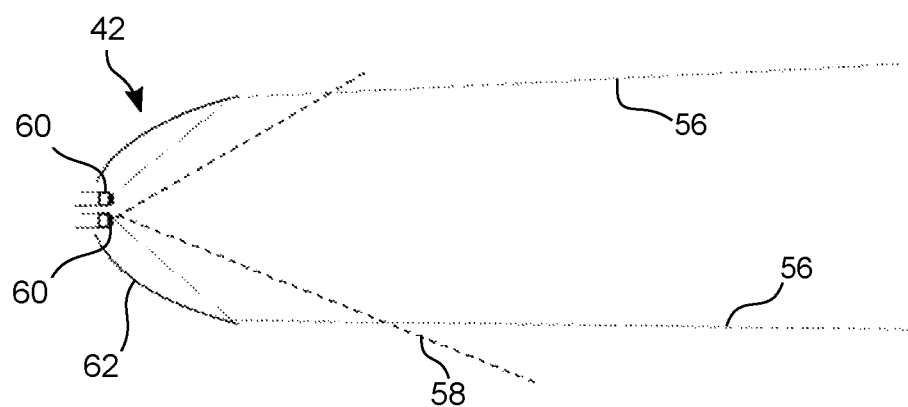
FIG. 5 shows a further radiating device in a sectional view.
Figure 6:
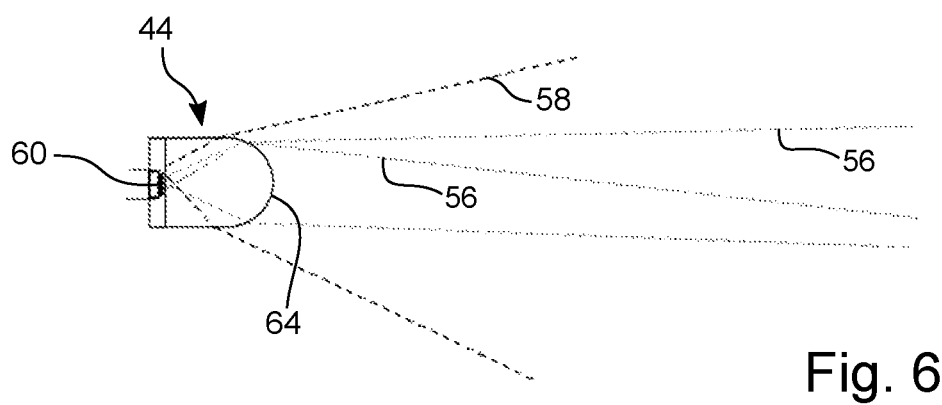
FIG. 6 shows a further radiating device in a sectional view.

FIGS. 4 to 6 show examples of differently designed radiating devices 40, 42, 44 comprising one or several radiation sources 60. FIGS. 4 to 6 show, for example, several ray paths 56, 58 of the radiation emanating from radiation sources 60.

FIGS. 4 and 5 show radiation sources 60 which are arranged in a reflector 62 designed as a concave mirror, wherein the radiating devices 40, 42 shown in FIGS. 4 and 5 can be designed as injector radiators. The radiation emanating from the radiation sources 60 is fed into the reflector 62 with as little loss as possible, wherein a directed bundle of rays is formed by reflection at the reflector 62 designed as a concave mirror. The object of such radiating devices is to shape the radiation emanating from one or several radiation sources placed closely next to each other into a bundle of rays that is as parallel as possible with as little loss as possible. The radiation direction of the bundle of rays emitted by the radiating device 40, 42 is directed away from the reflector 62. However, the primary radiation direction of the radiation sources 60 in the two exemplary radiating devices 40 and 42 is opposite to one another.

In the case of the radiating device 40 shown in FIG. 4, a very high proportion of the radiation emanating from the radiation source 60 is directed directly into the reflector 62, which is preferably designed as a parabolic mirror, and is then reflected from there.

In the case of the radiating device 42 shown in FIG. 5, the concave mirror of the reflector 62, which is also preferably designed as a parabolic mirror, is more strongly curved in comparison to FIG. 4. In contrast to FIG. 4, according to FIG. 5 the radiation direction of the radiation sources 60 is directed mainly directly out of the reflector 62. In FIG. 5, therefore, not all of the radiation emitted by the radiation sources 60 is reflected by the reflector 62 in the radiation direction.

FIG. 6 shows a radiating device 44 with a radiation source 60 and with a lens body 64. The lens body 64 is designed to be radiolucent and, in the example shown, forms a housing for the radiation source 60. The radiation emitted by the radiation source 60 is refracted at the lens body 64. In order to achieve an appropriate and good beam shaping, the lens body 64 must be correspondingly large and/or the emission area of the radiation source 60 correspondingly small. The exemplary design shown in FIG. 6 is foremost particularly cost-effective in the visible wavelength range of the light. In the UVC wavelength range, this is currently only true to a limited extent, although progress is expected here which will also make such a design possible for the UVC wavelength range.

The emission angle of the radiating devices 42, 44 shown in FIGS. 5 and 6 is greater than the emission angle of the radiating device 40 shown in FIG. 4. In the drawings, this comparison is made particularly clear by the exemplary ray paths 58, each indicated by a dashed line. The greater emission angle of the radiating devices 42, 44 shown in FIGS. 5 and 6 leads to higher losses on the inner walls of the shell or of the middle part of the pressure vessel 12 respectively. To counteract these losses, the number of radiating devices 42, 44 used in the disinfection device 10 can be increased. Alternatively or additionally, as already described above in connection with FIG. 2, the inner wall of the shell of the pressure vessel 12 can be equipped with a corresponding reflection surface 52.

The disinfection devices 10 described above on the basis of FIGS. 2 and 3 are indeed less powerful compared to a disinfection device 10 as shown as an example in FIG. 1 due to higher losses. A lower power is usually also still given despite providing at least one suitable reflection surface 52 on the inner wall of the shell of the pressure vessel 12. Nevertheless, the disinfection devices 10 described here with a tubular pressure container 16, 18 are sufficient for reduced volume flows and can be manufactured with comparatively little effort and a smaller diameter. Reduced volume flows can occur, for example, at individual treatment devices 80 or also in a connection line 76.

By employing one or several radiating devices shown as an example in FIG. 6 without their own reflector or parabolic reflector respectively, no improvement of the beam guidance can usually be achieved, however, the manufacturing costs of the disinfection device 10 can be reduced.

One or several radiating devices 40, which are designed according to the embodiment shown in FIG. 4, can be advantageously employed in a disinfection device 10 according to the embodiment shown in FIG. 1. The reflector 62 of the radiating device 40 is preferably designed as a parabolic mirror with at least one radiation source 60 arranged in the focal point, which radiates into the parabolic mirror. A UVC LED is preferably used as the radiation source 60. The parabolic mirror can, for example, have a spherical conicity of −1. The aperture radius of the parabolic mirror can, for example, be selected such that the aperture area of the reflectors 62 of all the radiating devices 40 used is preferably less than approximately 20%, and furthermore preferably less than 3% of the aperture area of the reflection surface 35, designed as a concave mirror, on the inner side of the bottom part 26 of the pressure vessel 12. The spherical radius is advantageously adjusted so that relatively little radiation loss occurs at the cylindrical surface of the pressure vessel 12.

The installation position of the radiating devices 40 is preferably near a reflection surface 35, located at an end, of the pressure vessel 12. The radiation of the radiating devices 40 is preferably directed nearly parallel to the longitudinal axis of the pressure vessel 12 onto the opposite reflection surface 34.

Since, in the overall arrangement, a loss of the radiation reflected back from the opposite reflection surface 34 when it impinges the same or another radiating device 40 can be minimized by a slight deviation from this parallelism, and at the same time a less concentrated, i.e. better distributed, irradiation of the air volume can occur, it can be advantageous to arrange at least one radiating device 40 outside the longitudinal axis of the pressure vessel 12. In order to achieve better irradiation of the entire interior space 50, it may also be advantageous to provide several radiating devices 40 in the pressure vessel 12.

Preferably, at least one radiating device 40 can be arranged outside the longitudinal axis of the pressure vessel 12. Furthermore, preferably, the same odd number of non-opposing radiating devices 40 can be provided at each reflecting surface 34, 35 formed as a concave mirror. Furthermore, two radiating devices 40 can preferably be provided at an angular position of 90°+/−45° with respect to the longitudinal axis of the pressure vessel 12. Furthermore, three radiating devices 40, for example, can preferably be provided at a reflecting surface 34, 35 formed as a concave mirror. The radiating devices 40 can preferably be arranged decentrally with a distance of approximately 0.25 times to approximately 0.75 times, preferably approximately 0.6 times the radius of the aperture of the concave mirror forming the reflection surface 34, 35 outside the longitudinal axis of the pressure vessel 12.

The radiating devices 40 radiate in general nearly parallel to the longitudinal axis of the pressure vessel 12, preferably however slightly tilted in the direction of the longitudinal axis, corresponding to the concave mirror curvature, and further preferably with a directional component tangential to the cylinder shell, so that a better circular irradiance through the interior space 50 is effected and radiation losses of the secondary ray by impingement on surfaces of the at least one radiating device 40 are reduced.

The at least one radiating device 40 can be arranged inside the concave mirror of a bottom part 26, wherein preferably the outer edge of the reflector 62 of the radiating device 40 can be arranged on the surface of the concave mirror. The concave mirror and the bottom part 26 connected to the concave mirror can thereby comprise an opening in this region for inspection and/or repair purposes.

In the case of a disinfection device 10 with a tubular pressure container 16, 18, as shown for example in FIGS. 2 and 3, the reflector 62 (see FIGS. 2 to 5) of the radiating device 42, 46, the reflector 62 being designed as a concave mirror, can preferably be dimensioned such that the aperture of the reflector 62 is approximately 0.5 to approximately 2 times the radius of the reflector 62, wherein the conicity of the reflector 62 can be approximately −1. In both cases, the reflector 62 can therefore be designed at least approximately as a parabolic mirror.

The radius R of the concave mirror formed by the reflection surface 36, 38 in the end part 30, 32 of the pressure vessel 12 can preferably be dimensioned as radius R=L/x, wherein L corresponds to the length of the pressure vessel 12 and x is, for example, in a range between −0.1 and +1.0, preferably between approximately +0.2 and approximately 1.0.

Preferably, a disinfection device 10 with a tubular pressure container 16, 18 can be equipped with one to five or more radiation sources 60. The radiation sources 60 can thereby be designed as LEDs or LED chips, for example. The radiation sources 60 can, for example, be arranged centrally or in a circle with a radius r around the longitudinal axis of the tubular pressure container 16, 18. The radius r can preferably and approximately be determined as r<0.3 R as a function of the radius R of the concave mirror. The distance d of the at least one radiation source 60 from the concave mirror in the direction of the longitudinal axis of the pressure container 16, 18 can, for example, be determined as approximately 0.5 R as a function of the radius R of the concave mirror.

The radiation sources 60 employed in the radiating devices 40, 42, 44, 46 emit preferably UV radiation. The disinfection according to the invention is particularly effective when radiation with wavelengths between approximately 200 nm and approximately 300 nm is emitted. Such radiation has a strong bactericidal effect. It is absorbed by the DNA, destroys its structure and inactivates living cells. Bonds within the DNA strands of viruses, bacteria and mould spores are destroyed by the radiation. Microorganisms such as viruses, bacteria, yeasts and fungi can be rendered harmless by UV radiation in a short time. UV disinfection is particularly reliable with sufficiently high irradiation intensity. In addition, microorganisms cannot develop resistance to UV rays.

Since no chemicals are used to disinfect the air during irradiation, this type of disinfection is environmentally friendly. It is also harmless to persons if the persons present are shielded from the radiation. Reliable shielding can, for example, already be provided by the housing of the pressure vessel 12.

The pressure vessel 12 comprises materials which are stable against the radiation emitted by the radiation sources 60.

Furthermore, the radiation sources 60 preferably emit UVC radiation. UVC radiation is particularly suitable for air disinfection. When UVC radiation impinges on microorganisms, their DNA is changed within a very short time so that reproduction is no longer possible. In this way, viruses and germs such as MRSA, SARS, Corona or H7N9 can be eliminated especially quickly and effectively. The effective wavelength range is preferably between approximately 250 nm and approximately 280 nm.

Thus, for example, the air contained in a compressed air tank can be sterilized with the aid of UVC radiation by reaching and killing microorganisms floating in the air as well as those on the inner wall of the tank by the UVC radiation. The radiation dose required to kill microorganisms and viruses, is, for example, between approximately 2.5-5.0 mW sec/cm$^2$ (for *Staphylococcus aureus*) and approximately 34 mW sec/cm$^2$ (for the hepatitis virus).

Figure 7:
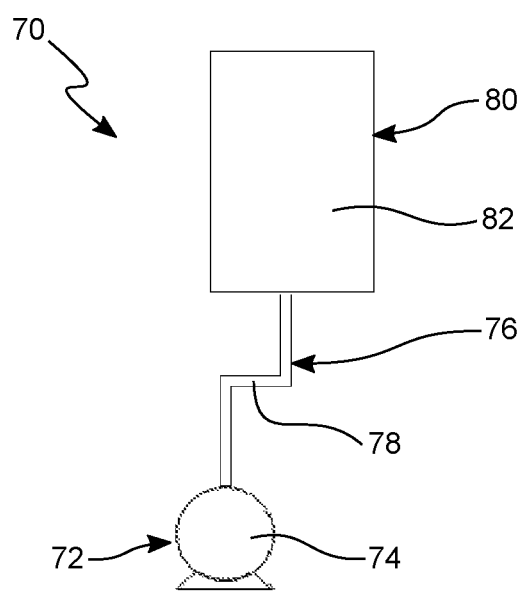
FIG. 7 shows a compressed air system in a very simplified schematic view.

FIG. 7 shows an example of a compressed air system for medical or dental applications. A compressor 72 is shown here in a schematic illustration, wherein the compressor 72 is connected via a connection line 76, for example a tube, to a treatment device 80, for example a dental chair. A disinfection device 10 according to the invention can, for example, be provided for air disinfection in the pressure tank 74 of the compressor 72. Alternatively or additionally, the treatment device 80 can be equipped with one or several compressed air devices 82 which comprise a disinfection device 10 according to the invention. Alternatively or additionally, the connection line 76 can comprise one or several tube sections 78 with a disinfection device 10 according to the invention.

Disinfection devices 10 can be provided once or several times in a connection line 76 and/or in a treatment device 80. A disinfection device 10 can thereby also be used as an additional buffer for air to be disinfected, if it is dimensioned accordingly. In this way it can be ensured that even temporary, i.e. relatively short, peak flows of the medium can be reliably disinfected. A suitable dimensioning for providing such a buffer can already be achieved by a relatively small enlargement of the diameter of a tubular pressure container 16, 18.

To increase performance, several disinfection devices 10 can be arranged in series or parallel, for example.

The disinfection devices 10 described based on the embodiments are particularly suitable for the disinfection of compressed air in compressed air accumulators or compressed air vessels respectively in medicine or dental medicine. A disinfection device 10 according to the invention can also be employed for the disinfection of other media such as liquids. If necessary, appropriate design modifications may be appropriate. A prerequisite for the effectiveness of the disinfection device 10 is that the range of the radiation in the medium is sufficiently large, taking into account the dimensions of the pressure vessel 12.

A compressed air accumulator for dental treatment air can, for example, be arranged inside or outside of a dental treatment device 80, e.g. a treatment chair or a chair module, depending on parameters such as air consumption, radiation intensity and overall size.

One or several UVC LEDs, which preferably emit radiation with a wavelength range from approximately 250 nm to approximately 280 nm, can be particularly advantageously provided as radiation sources 60. The radiation sources 60 designed as UVC LEDs are each arranged at a suitable position in a compressed air accumulator and emit their radiation into a reflection device which is designed such that the radiation passes through distance sections, which are as long as possible, to the next reflection. Radiation losses caused by a reflection can be reduced by travelling distance sections that are free of radiation reflection as long as possible. In this way, an effect multiplier of approximately 3 to 8 (or even higher if better reflectors are available) can be achieved in the disinfection device 10, whereby the number of UVC LEDs required for irradiation is considerably reduced.

In order to ensure reliable disinfection, it is necessary that all air layers and surfaces within the pressure vessel 12 are covered by the radiation range of the UVC radiators. The residence time of the medium in the pressure vessel 12 and the radiation intensity must be coordinated to each other in such a way that the radiation dose necessary for the certain destruction of any microorganisms in the medium is achieved as continuously as possible.

The use of currently available UVC light-emitting diodes also significantly increases costs and effort with higher radiation power. The use of mercury vapour lamps as radiation sources, which are commonly used in various other fields of application and known in themselves, is not desirable in a pressure vessel for compressed air used, in the case of dental patients, in the oral cavity.

In the case of disinfection devices 10, as shown in FIGS. 1 to 3 as an example, it can at least be largely avoided that radiation emitted by a radiation source 60 is absorbed to a large extent uselessly on the container wall of the pressure vessel 12, the container wall located opposite the radiation sources 60. The highest degree of efficiency for the disinfection is achieved when each ray emitted by a radiation source 60 covers the greatest possible distance, or passes through the greatest possible amount of air unhindered respectively before it is completely absorbed. The air compressed in a pressure vessel is thus already a multiplier for the efficiency of the disinfection. Using this principle recognized by the inventors, even the amount of radiation of a relatively small UVC LED can kill a significantly larger amount of germs in a relatively short time than would be expected without taking this principle into account.

The type and number of UVC LEDs to be provided in a pressure vessel 12 in appropriate fashion may be determined taking into account parameters such as tank size, pressure, flow rate and air extraction. The air extraction thereby affects, for example, the average residence time of the air in a compressed air tank.

In the case of the disinfection devices described above, the aim is to design the interior of a compressed air container reflective as advantageously as possible and to achieve an arrangement of the UVC LEDs that is as advantageous as possible, in order to achieve a multiple reflection in conjunction with an air mass located therebetween that is as large as possible for the radiation emitted by the UVC LEDs. This is therefore particularly important for the effectiveness of the disinfection device 10, as the radiation loss for each reflection can be up to approximately 10% with the currently available materials.

If a parallel light beam is sent back and forth between two reflectors as often as desired, then the maximum achievable integral radiation gain corresponds to the factor of the reciprocal value of the reflection loss of the reflection surface. Due to the multiplication of the radiation effect according to the invention, an economic and reliable implementation of an air disinfection in pressure vessels using UVC LEDs is made possible. It is thus, for example, possible to achieve a sufficient effect for a large number of applications, for example, with a single-digit number of UVC LEDs.

In an alternative design, laser diodes can also be used as one or several radiation sources, preferably with an emission wavelength in the range between approximately 250 nm and approximately 280 nm. The advantage of using laser diodes is that the laser light can be used in an even more targeted fashion. However, laser diodes in this wavelength range are still in development and are not readily available for industrial applications.

An idea on which the invention is based can be summarized as follows: The invention relates to a disinfection device 10 with a pressure vessel 12 which comprises an interior space 50 for receiving a medium, and with at least one radiating device 40, 42, 44, 46 which is arranged such that it emits radiation into the interior space 50 of the pressure vessel 12, wherein one or several surfaces of the interior space 50 of the pressure vessel 12 are formed at least partially as reflection surface 34, 35, 36, 37, 38, 39, 52 for the radiation. According to the invention, a particularly reliable disinfection of medical or dental compressed air in the pressure vessel 12 is made possible. One or several disinfection devices 10 according to the invention can be provided in a compressor 72 for providing compressed air for dental applications, in a dental treatment device 80 with a compressed air device 82 and/or in a connection device with one or several tube sections 78 for guiding compressed air for dental applications. Further advantages of the disinfection devices 10 according to the invention are among others: reduction of taste and smell impairment, avoidance of the formation of health-endangering by-products, possible dispensing with the use of mercury for radiation generation, possible dispensing with the addition of chemicals for disinfection, low maintenance requirements and easy handling, low operating costs, very high operational reliability.

While this invention is susceptible to embodiments in many different forms, there is described in detail herein, preferred embodiments of the invention with the understanding that the present disclosures are to be considered as exemplifications of the principles of the invention and are not intended to limit the broad aspects of the invention to the embodiments illustrated.

What is claimed is:

1. A disinfection device with at least one radiating device, comprising:
   a pressure vessel with an interior space for receiving a medium;
   at least one radiating device arranged such that it emits radiation into the interior space, wherein a first surface of the interior space is formed at least partially as a first reflection surface, and a second surface of the interior space is formed at least partially as a second reflection surface,
   wherein the first surface is located opposite the second surface within the interior space, wherein the at least one radiating device is arranged such that a principal direction component of the emitted radiation is aligned parallel to a longitudinal axis of the pressure vessel, and
   wherein the at least one radiating device is arranged in a region of a first side of the interior space, and in that a second side, opposite this first side, of the interior space comprises the second reflection surface.

2. The disinfection device according to claim 1, wherein the at least one radiating device comprises a UVC radiation source.

3. The disinfection device according to claim 1, wherein the at least one radiating device comprises an LED as a radiation source.

4. The disinfection device according to claim 3, wherein the radiation source of the radiating device is arranged in a concave mirror.

5. The disinfection device according to claim 1, wherein at least one additional reflection surface is formed in the interior space.

6. The disinfection device according to claim 1, wherein at least one of the first reflection surface or the second reflection surface is formed in the form of a concave mirror.

7. The disinfection device according to claim 1, wherein at least one of the first reflection surface or the second reflection surface is formed by a reflection layer applied to a substrate.

8. The disinfection device according to claim 1, wherein the pressure vessel is designed as a tank with at least one passage for inflow and outflow of the medium.

9. The disinfection device according to claim 1, wherein the pressure vessel is configured as a compressed air vessel for dental compressed air.

10. A compressor system for providing compressed air for dental applications, comprising a compressor system which comprises the disinfection device according to claim 1.

11. A dental treatment device with a compressed air device, comprising a compressed air device which comprises the disinfection device according to claim 1.

12. A connection device with one or several tube sections for guiding compressed air for dental applications, comprising at least one tube section which comprises the disinfection device according to claim 1.

13. The disinfection device according to claim 1, wherein the first reflection surface reflects radiation towards the second reflection surface and the second reflection surface reflects radiation towards the first reflection surface.

14. The disinfection device according to claim 1, wherein the at least one radiating device is arranged at a focal point of the first reflection surface.

15. The disinfection device according to claim 1, wherein the pressure vessel is dimensioned as a radius $R=L/x$, wherein L is a length of the pressure vessel and x is in a range between −0.1 and +1.0.

16. The disinfection device according to claim 1, wherein the at least one radiating device comprises a plurality of radiating devices, wherein the plurality of radiating devices are arranged in a circle with a radius r around the longitudinal axis of the pressure vessel.

17. The disinfection device according to claim 16, wherein the plurality of radiating devices are arranged in a concave mirror, wherein the radius r is less than a dimension of 0.3 R, wherein R is a radius of the concave mirror.

18. The disinfection device according to claim 6, the first reflection surface is formed in the form of a concave mirror, the disinfection device further comprising at least one reflector formed as a parabolic mirror in a portion of the concave mirror, and wherein the at least one radiating device is arranged in a focal point of the parabolic mirror.

19. The disinfection device according to claim 18, wherein an aperture radius of the parabolic mirror is less than approximately 20% of an aperture area of the concave mirror.

20. The disinfection device according to claim 18, wherein an aperture radius of the parabolic mirror is less than 3% of an aperture area of the concave mirror.

* * * * *